(12) United States Patent
Kristen et al.

(10) Patent No.: US 6,559,326 B1
(45) Date of Patent: May 6, 2003

(54) SUBSTITUTED PHOSPHINOPHENOXIDE-METAL COMPLEXES FOR THE POLYMERIZATION OF OLEFINS

(75) Inventors: Marc Oliver Kristen, Limburgerhof (DE); Joachim Heinicke, Wackerow (DE); Wilhelm Keim, Aachen (DE); Martin Koehler, Greifswald (DE); Mengzhen He, Greifswald (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 227 days.

(21) Appl. No.: 09/712,282

(22) Filed: Nov. 15, 2000

(30) Foreign Application Priority Data

Nov. 17, 1999 (DE) .......................... 199 55 454

(51) Int. Cl.$^7$ .......................... C07F 9/50; B01J 31/00; C08F 110/02

(52) U.S. Cl. .......................... 556/21; 556/12; 556/18; 556/23; 556/30; 556/137; 556/150; 526/139; 526/145; 526/192; 526/193; 526/348; 526/352; 502/117; 502/155

(58) Field of Search .......................... 556/12, 18, 21, 556/23, 30, 137, 150; 502/117, 155; 526/139, 145, 192, 193, 348, 352

(56) References Cited

U.S. PATENT DOCUMENTS

| | | | |
|---|---|---|---|
| 3,635,937 A | 1/1972 | Bauer et al. ................... | 260/94 |
| 4,404,344 A | 9/1983 | Sinn et al. ................... | 526/160 |
| 4,472,522 A | 9/1984 | Singleton ................... | 502/108 |
| 4,472,525 A | 9/1984 | Singleton ................... | 502/155 |
| 4,503,279 A | 3/1985 | Singleton ................... | 585/523 |
| 4,620,021 A | 10/1986 | Starzewski et al. ........... | 556/19 |

FOREIGN PATENT DOCUMENTS

| | | |
|---|---|---|
| DE | 34 45 090 | 6/1986 |
| WO | WO 96/23010 | 8/1996 |

OTHER PUBLICATIONS

Heinicke et al., Zeitschrift fuer Naturforschung, B: Chemical Sciences, vol. 54, No. 10, pp. 1235–1243 (Oct. 1999).*
Echte et al. "Homogene Polyreaktionen" (1993) pp. 301–303.
Keim et al. "Reactions of Chelate Ylides with Nickel(O) Complexes" Organometallics vol. 5 (1986) pp. 2356–2359.
Pietsch et al. "Niclek Phenyl complexes with chelating K$^2$–P, O ligands as catalysts for the oligomerization of ethylene into linear α–olefins" New J. Chem. (1998) pp. 467–472.
U. Jux "Synthese und Eigenschaften PH–funktionneller o–Hydroxyarylphosphane"(1996) pp. 45–46.
Elschenbroich et al. "Organometallchemie"(1990) pp. 235–241 and 258–291.

Heinicke et al. "P/O Ligand Systems: Synthesis and Reactivity of Primary and Secondary o–Phosphinophenols" Heteroatom Chemisty vol. 8, No. 5 (1997) pp. 383–396.

Heinicke et al. "Sterically Stressed Amino– and PH–Functional Di–t–butyl–o–phosphihophenols–Intramolecular Interaction and Formation of Benzoxadiphospholes" Heteroatom Chemistry vol. 9, No. 2 (1998) pp. 183–193.

T. Rauchfuss "o–Diphenylphosphinophenol and Its Coordination Compounds" Inorganic Chemistry, vol. No. 11 (1997) pp. 2966–2968.

Heinicke et al. "Synthese und Umlagerungsreaktion von o–Funktionellen Phenyllithium–und Phenylnatrium Derivaten Der IVB–Und VB–Elemente" Journal of Organometallic Chemistry, vol. 243 (1993) pp. 1–8.

Heinicke et al. "Syntheses, Structures and Reactivity of 1–Phosphanylnaphth–2–ols" Chem. Ber. vol. 129 (1996) pp. 1061–1071.

(List continued on next page.)

*Primary Examiner*—Porfirio Nazario-Gonzalez
(74) *Attorney, Agent, or Firm*—Keil & Weinkauf

(57) ABSTRACT

Metal complexes obtainable from a metal precursor of a metal of the 6$^{th}$–10$^{th}$ groups of the Periodic Table in the oxidation state 0 or +2 and a ligand of the formula I,

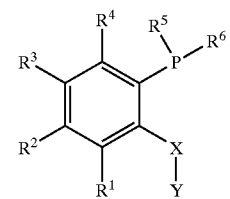

I where the radicals are defined as follows:

$R^1$, $R^2$ and $R^4$ are hydrogen, $C_1$–$C_{12}$-alkyl groups, $C_3$–$C_{12}$-cycloalkyl groups, $C_6$–$C_{14}$-aryl groups, $C_2$–$C_{12}$-alkenyl groups, arylalkyl groups, halogens, silyl groups, $C_1$–$C_{12}$-alkoxy groups, $C_1$–$C_{12}$-thioether groups or amino groups;

$R^3$ is an α-branched $C_3$–$C_{12}$-alkyl group or a substituted or unsubstituted $C_3$–$C_{12}$-cycloalkyl group, a $C_2$–$C_{12}$-alkenyl group, an arylalkyl group, a halogen, a silyl group, a $C_1$–$C_{12}$-alkoxy group, a $C_1$–$C_{12}$-thioether group or an amino group;

X is oxygen, sulfur,

Y is hydrogen or a silyl group, $R^5$ to $R^6$ are α-branched $C_3$–$C_{12}$-alkyl groups or substituted or unsubstituted $C_3$–$C_{12}$-cycloalkyl groups;

can be used in free form or immobilized on a solid support for the polymerization of 1-olefins.

14 Claims, No Drawings

OTHER PUBLICATIONS

Heinicke et al. "P/O Ligand Systems: Synthesis, Reactivity, and Structure of Tertiary o–Phosphanylphenol Derivatives" Chem Ber. vol. 129 (1996) pp. 1547–1560.

Stache "TEnsid Taschenbuch" (1981) pp. 672–679.

McCutcheon's Emulsifiers & Detergents (1989) pp. 207–240.

Heinicke et al. "Methyl(2–phophanylphenolato[P,O])nickel(II) Complexes–Synthesis, Structure, and Activity as Ethene Oligomerization Catalysts" Eur. J. Inorg. Chem. (2000) pp. 431–440.

Heinicke et al. "o–Hydroxyarylphosphines and diphosphines: metallation–rearrangement versus P–O reduction of o–halogenoaryloxy phosphines by sodium" Journal of Organometallic Chemistry vol. 520 (1996) pp. 131–137.

Heinicke et al. "o–Phosphinopehnoles–Synthesis and Reactivity" Phosphorus, Sulfur and Silicon, vols. 109–110 (1996) pp. 501–504.

Fox et al. "Synthesis and Electrochemical Activity of Nickel Phosphine Complexes and Polymers Bound to Electrode Surfaces" Macromolecules vol. 24 (1991) pp. 4626–4636.

* cited by examiner

SUBSTITUTED PHOSPHINOPHENOXIDE-METAL COMPLEXES FOR THE POLYMERIZATION OF OLEFINS

Substituted phosphinophenoxide-metal complexes for the polymerization of olefins.

The present invention relates to novel phosphinophenoxide-metal complexes for the polymerization of 1-olefins. The invention further relates to catalysts comprising the novel phosphinophenoxide-metal complexes, a process for the polymerization of 1-olefins using the novel complexes and also the polymers and moldings obtainable in this way.

The metal complexes are obtainable from a metal precursor of a metal of the $6^{th}$–$10^{th}$ groups of the Periodic Table in the oxidation state 0 or +2 and a ligand of the formula I,

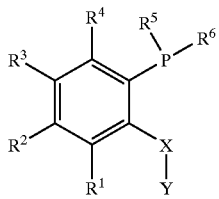

I where $R^1$, $R^2$ and $R^4$ are, independently of one another:
  hydrogen,
  $C_1$–$C_{12}$-alkyl,
  $C_1$–$C_{12}$-alkyl bearing one or more identical or different $C_1$–$C_{12}$-alkyl groups, halogens,
  $C_1$–$C_{12}$-alkoxy groups or $C_1$–$C_{12}$-thioether groups as substituents,
  $C_7$–$C_{20}$-arylalkyl,
  $C_2$–$C_{12}$-alkenyl,
  $C_3$–$C_{12}$-cycloalkyl,
  $C_3$–$C_{12}$-cycloalkyl bearing one or more identical or different $C_1$–$C_{12}$-alkyl groups, halogens,
  $C_1$–$C_{12}$-alkoxy groups or $C_1$–$C_{12}$-thioether groups as substituents,
  $C_6$–$C_{14}$-aryl,
  $C_6$–$C_{14}$-aryl bearing one or more identical or different $C_1$–$C_{12}$-alkyl groups, halogens,
  monohalogenated or polyhalogenated $C_1$–$C_{12}$-alkyl groups, $C_1$–$C_{12}$-alkoxy groups, silyloxy groups $OSiR^7R^8R^9$, amino groups $NR^{10}R^{11}$ or $C_1$–$C_{12}$-thioether groups as substituents,
  $C_1$–$C_{12}$-alkoxy groups,
  $C_6$–$C_{14}$-aryloxy groups,
  $C_1$–$C_{12}$-thioether groups,
  silyloxy groups $OSiR^7R^8R^9$,
  halogens
  or amino groups $NR^{10}R^{11}$;

$R^3$ is selected from among the following groups:
  α-branched $C_3$–$C_{12}$-alkyl groups,
  $C_1$–$C_{12}$-alkyl bearing one or more identical or different $C_1$–$C_{12}$-alkyl groups, halogens,
  $C_1$–$C_{12}$-alkoxy groups or $C_1$–$C_{12}$-thioether groups as substituents in the α position,
  $C_7$–$C_{20}$-arylalkyl,
  $C_2$–$C_{10}$-alkenyl,
  $C_3$–$C_{10}$-alkenylalkyl having at least one double bond, where at least one C—C double bond is conjugated with the aromatic,
  $C_3$–$C_{12}$-cycloalkyl,
  $C_6$–$C_{14}$-aryl,
  $C_6$–$C_{14}$-aryl bearing one or more identical or different $C_1$–$C_{12}$-alkyl groups, halogens, monohalogenated or polyhalogenated $C_1$–$C_{12}$-alkyl groups, $C_1$–$C_{12}$-alkoxy groups, silyloxy groups $OSiR^7R^8R^9$, amino groups $NR^{10}R^{11}$ or $C_1$–$C_{12}$-thioether groups as substituents,
  $C_1$–$C_{12}$-alkoxy groups,
  $C_6$–$C_{14}$-aryloxy groups,
  $C_1$–$C_{12}$-thioether groups,
  silyloxy groups $OSiR^7R^8R^9$,
  halogens
  and amino groups $NR^{10}R^{11}$,
  where in each case adjacent radicals $R^1$ to $R^4$ may together form a 5- to 8-membered ring;

$R^5$ and $R^6$ are selected independently from among
  α-branched $C_3$–$C_{12}$-alkyl groups,
  $C_3$–$C_{12}$-cycloalkyl groups,
  $C_3$–$C_{12}$-cycloalkyl groups bearing one or more identical or different $C_1$–$C_{12}$-alkyl groups,
  halogens, monohalogenated or polyhalogenated $C_1$–$C_{12}$-alkyl groups, $C_1$–$C_{12}$-alkoxy groups,
  silyloxy groups $OSiR^7R^8R^9$, amino groups $NR^{10}R^{11}$ or $C_1$–$C_{12}$-thioether groups as substituents, X is oxygen, sulfur, selenium, N—$R^{12}$, P—$R^{12}$ or $AsR^{12}$, Y is hydrogen or
  an alkali metal cation,
  a $C_1$–$C_{18}$-alkylacyl anion,
  a $C_6$–$C_{14}$-arylacyl anion or $SiR^7R^8R^9$, $R^7$ to $R^{12}$ are selected independently from among hydrogen, branched or unbranched $C_1$–$C_6$-alkyl groups, benzyl radicals and $C_6$–$C_{14}$-aryl groups, where in each case two adjacent radicals $R^7$ and $R^8$ or $R^{10}$ and $R^{11}$ may together form a saturated or unsaturated 5- to 8-membered ring.

Polyolefins are of general importance as materials, for example for producing films or sheets, fibers or hollow bodies, for example bottles.

New improved processes for preparing polyolefins are therefore of great economic importance. The type of catalysts used is particularly important in this respect.

Conventional processes and catalysts such as Ziegler-Natta catalysts (e.g. A. Echte, Lehrbuch der technischen Polymerchemie, VCH, Weinheim, New York, Basle, Cambridge, Tokyo; 1993; pp. 301–3) and metallocenes (e.g. DE-A 30 07 725) frequently have the disadvantage that aluminum alkyls have to be used for activating them. These are extremely sensitive to moisture and to Lewis bases, so that the activity of the catalysts is greatly reduced by any contaminated monomers. In addition, some aluminum alkyls represent a fire hazard.

The nickel complexes described in WO 96/23010 also have to be activated by means of aluminum alkyls or Lewis acids based on borane.

U.S. Pat. No. 4,472,522 and U.S. Pat. No. 4,472,525 disclose nickel complexes having the structure A,

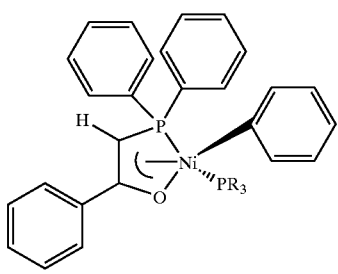

A which can be activated without aluminum alkyl. These are suitable for the oligomerization of ethylene to give 1-olefins (SHOP process). This compound was converted into derivatives in various ways. Despite variation of the radicals R (see W. Keim et al., Organometallics 1986, 5, 2356–9), it was not possible to produce suitable materials since the molar masses obtained are too low.

Furthermore, U.S. Pat. No. 4,472,525 discloses a catalyst system comprising ortho-diethylphosphinophenol A' or ortho-diphenylphosphinophenol A",

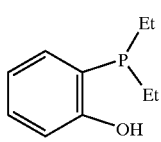

A' which after reaction with Ni(COD)$_2$ in situ with ethylene gives linear oligomers, but no polymers which can be used as polymeric materials.

Braunstein et al. attempted to influence the yield and structure by changing the electron density on the chelating phosphorus.

They used the ortho-phosphinophenol derivative B

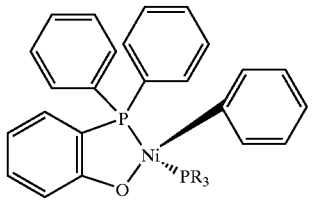

B (J. Pietsch, P. Braunstein, Y. Chauvin, *New J. Chem.* 1998, 467). The products of the reaction of ethylene and compound B were likewise linear 1-olefins having an average degree of oligomerization of 40.

U.S. Pat. No. 3,635,937 discloses selected Ni complexes, for example B',

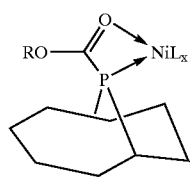

B' where R=methyl or ethyl and L$_x$ may be a 1,5-cyclooctadiene, which are able to polymerize ethylene to polyethylene without activation by an aluminum alkyl. The molecular weights M$_w$ are, at from about 95,000 to 162,000, very attractive, but the activities of 0.73 kg of PE/mol of Ni·h (Example II) are too low for industrial applications.

DE-A 33 36 500 and DE-A 34 45 090 disclose Ni catalysts which can be obtained in situ from a tertiary phosphine, a quinoid compound and an Ni(O) compound or a precursor which can readily be reduced to an Ni(O) compound. Although they polymerize ethylene to polyethylene, their preparation requires very air- and moisture-sensitive Wittig reagents as precursors, which is disadvantageous for industrial applications.

In his thesis, U. Jux (U. Jux, Thesis at the University of Greifswald, 1996) showed that it is possible to prepare polyethylene using Ni complexes of the compounds C, C' and C" without prior activation by means of an aluminum alkyl.

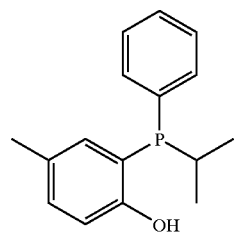

C

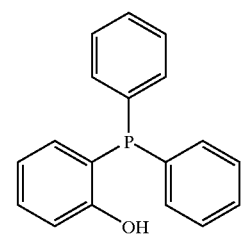

However, the activities of 1.4 kg of PE/mol of Ni·h (compound C), 1.4 kg of PE/mol of Ni·h (compound C') and 2.1 kg of PE/mol of Ni·h (compound C") were still too low for industrial applications.

At the GDCh conference in Munich (Aug. 16–21, 1998, cf. conference proceedings, poster B197), further Ni complexes which are likewise able to polymerize ethylene without prior activation by means of an aluminum alkyl were disclosed. Ligands of the formulae D, D' and D" were tested.

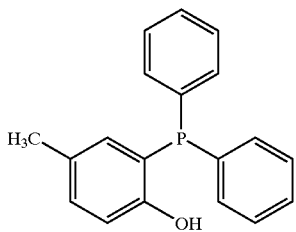
D

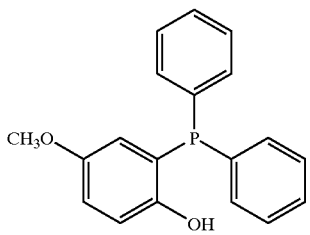
D'

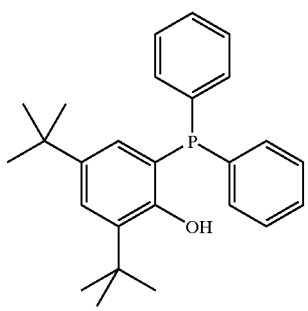
D''

These compounds are all triarylphosphinophenols. However, the polymers obtained had molar masses of less than 10,000 g/mol, which is too low for practical materials. Ni complexes of the diarylmonoalkylphosphinophenols D''' and D''''

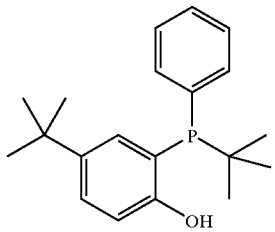
D'''

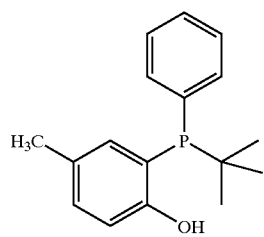
D'''' likewise displayed polymerization activity toward ethylene, but the molar masses were still below 10,000 g/mol and thus too low for applications as materials.

Finally, secondary phosphinophenol ligands ($R^6$ in formula I=H) which were reacted with $Ni(COD)_2$ and produced high molecular weight polyethylene were disclosed at the abovementioned GDCh conference. However, it was found that the secondary phosphinophenols were extremely sensitive toward the slightest traces of atmospheric oxygen. Our own experiments using these metal complex systems displayed poor reproducibility; a number of experiments under apparently identical conditions gave no polymer at all. In industrial-scale plants, however, it is important to have sufficiently robust catalyst systems.

It is an object of the present invention to provide a metal complex system which
- is able to polymerize 1-olefins at high activities without activation by means of aluminum alkyls;
- is sufficiently stable toward atmospheric oxygen to give reproducible results and thus be suitable for use in industrial plants, and, furthermore,
- gives polyolefins whose molar masses are high enough for them to be suitable for producing films, sheets, fibers or hollow bodies.

We have found that this object is achieved by the metal complexes described at the outset which are obtainable from a metal precursor of a metal of the $6^{th}$–$10^{th}$ groups of the Periodic Table in the oxidation state 0 or +2 and a ligand of the formula I and are suitable for polymerizing 1-olefins to give polymeric materials. Here, the choice of substituents on the ligand is critical.

In the metal precursors, use is made of metals M of the $6^{th}$–$10^{th}$ groups of the Periodic Table of the Elements, for example chromium, manganese, iron, cobalt, nickel and palladium. Preference is given to iron, cobalt, nickel and palladium, particularly preferably nickel. These metals are present in the oxidation state 0 or +2. These metals are stabilized by ligands.

As ligands of the metal precursors, it is possible to use the uncharged molecules customarily used in coordination chemistry (cf. Elschenbroich/Salzer, "Einführung in die Organometallchemie", $3^{rd}$ Edition, B. G. Teubner Verlag, Stuttgart 1990). Preference is given to aliphatic and aromatic phosphines $R_xPH_{3-x}$ and amines $R_xNH_{3-x}$ where x=0, 1, 2, 3 and R is selected from the group of radicals defined in more detail under $R^1$ (see below). However, CO, $C_1$–$C_{12}$-alkyl nitriles or $C_6$–$C_{14}$-aryl nitriles, e.g. acetonitrile, propionitrile, butyronitrile or benzonitrile, are also suitable. Further ligands which can be used are singly or multiply ethylenically unsaturated double bond systems such as ethenyl, propenyl, cis-2-butenyl, trans-2-butenyl, cyclohexenyl, norbornenyl, 1,5-cyclooctadienyl ligands ("COD"), 1,6-cyclodecenyl ligands, 1,5,9-all-trans-cyclododecatrienyl ligands, triphenylphosphine ligands and norbornadienyl ligands.

Also suitable are anionic ligands such as halide ions, e.g. fluoride, chloride, bromide or iodide, alkyl anions, e.g. $(CH_3)$—, $(C_2H_5)$—, $(C_3H_7)$—, $(n-C_4H_9)$—, $(tert-C_4H_9)$— or $(C_6H_{14})$—, allyl anions and benzyl anions and also aryl anions, e.g. the phenyl anion.

Particularly preferred ligands are ethene ligands, 1,5-cyclooctadienyl ligands ("COD"), 1,6-cyclodecenyl ligands, 1,5,9-all-trans-cyclododecatrienyl ligands, triphenylphosphine ligands and also norbornadienyl ligands. In these preferred cases, the corresponding metal precursor is $Ni(C_2H_4)_3$, $Ni(COD)_2$, $Ni(1,6\text{-cyclodecadiene})_2$, $Ni(1,5,9\text{-all-trans-cyclododecatriene})_2$, $Pd(norbornadiene)Cl_2$ and also $Ni[P(C_6H_5)_3]_4$ and $Pd[P(C_6H_5)_3]_4$.

Very particular preference is given to $Ni(COD)_2$.

If the metals M are present in the oxidation state +2, a reducing agent has to be added to generate the oxidation state 0 in situ. Suitable reducing agents are the compounds customary in organic and organometallic chemistry. Preferred reducing agents are NaH, KH, complex hydrides such as LiAlH$_4$, LiBH$_4$, NaBH$_4$, Na(CN)BH$_3$, (isobutyl)$_2$AlH, alkali metals such as Na, K or Na/K alloy and H$_2$. Particular preference is given to NaH.

The radicals R$^1$, R$^2$ and R$^4$ are, independently of one another:

hydrogen,

C$_1$–C$_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl, and n-dodecyl; preferably C$_1$–C$_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably C$_1$–C$_4$-alkyl such as methyl, ethyl, n-propyl, isopropyl, n-butyl, isobutyl, sec-butyl and tert-butyl;

C$_3$–C$_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl;

examples of substituted cycloalkyl groups are: 2-methylcyclopentyl, 3-methylcyclopentyl, cis-2,4-dimethylcyclopentyl, trans-2,4-dimethylcyclopentyl 2,2,4,4-tetramethylcyclopentyl, 2-methylcyclohexyl, 3-methylcyclohexyl, 4-methylcyclohexyl, cis-2,5-dimethylcyclohexyl, trans-2,5-dimethylcyclohexyl, 2,2,5,5-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,5,5-tetrachlorocyclohexyl, 2-thiomethylcyclopentyl, 2-thiomethylcyclohexyl, 3-thiomethylcyclopentyl, 3-thiomethylcyclohexyl and further derivatives;

C$_7$–C$_{20}$-aralkyl, preferably C$_7$–C$_{12}$-phenylalkyl such as benzyl, 1-phenethyl, 2-phenethyl, 1-phenylpropyl, 2-phenylpropyl, 3-phenylpropyl, neophyl(1-methyl-1-phenylethyl), 1-phenylbutyl, 2-phenylbutyl, 3-phenylbutyl and 4-phenylbutyl, particularly preferably benzyl, C$_2$–C$_{12}$-alkenyl, preferably C$_2$–C$_6$-alkenyl such as vinyl, 1-propenyl, isopropenyl, 1-butenyl, isobutenyl, sec-butenyl, buta-1,3-dienyl, n-pent-1-enyl, isopentenyl, sec-pentenyl, neopentenyl, isoprenyl, 1,2-dimethylpropenyl, n-hexenyl, isohexenyl, sec-hexenyl, particularly preferably C$_2$–C$_4$-alkenyl such as vinyl, 1-propenyl, isopropenyl, 1-butenyl, isobutenyl, sec-butenyl and buta-1,3-dienyl;

C$_6$–C$_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

C$_6$–C$_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl substituted by one or more C$_1$–C$_{12}$-alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl, and n-dodecyl; preferably C$_1$–C$_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably C$_1$–C$_4$-alkyl such as methyl, ethyl, n-propyl, isopropyl, n-butyl, isobutyl, sec-butyl and tert-butyl;

halogens such as fluorine, chlorine, bromine and iodine, with preference being given to chlorine and bromine, monohalogenated or polyhalogenated C$_1$–C$_{12}$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

C$_1$–C$_{12}$-alkoxy groups, preferably C$_1$–C$_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

silyloxy groups OSiR$^7$R$^8$R$^9$ where R$^7$ to R$^9$ are selected independently from among hydrogen, C$_1$–C$_6$-alkyl groups, benzyl radicals and C$_6$–C$_{14}$-aryl groups; preference is given to the trimethylsilyloxy, triethylsilyloxy, triisopropylsilyloxy, diethylisopropylsilyloxy, dimethylthexlsilyloxy, tert-butyldimethylsilyloxy, tert-butyldiphenylsilyloxy, tribenzylsilyloxy, triphenylsilyloxy and tri-para-xylylsilyloxy groups; particular preference is given to the trimethylsilyloxy group and the tert-butyldimethylsilyloxy group;

or amino groups NR$^{10}$R$^{11}$, where R$^{10}$ and R$^{11}$ are selected independently from among hydrogen, C$_1$–C$_6$-alkyl groups and C$_6$–C$_{14}$-aryl groups which may form a saturated or unsaturated 5–10-membered ring; preference is given to the dimethylamino, diethylamino, diisopropylamino, methylphenylamino and diphenylamino groups. Examples of amino groups having saturated rings are the N-piperidyl group and the N-pyrrolidinyl group; examples of amino groups having unsaturated rings are the N-pyrryl, N-indolyl and N-carbazolyl groups;

C$_1$–C$_{12}$-thioether groups such as methylthio, ethylthio, propylthio, 1-methylpropylthio, 1,1-dimethylethylthio, phenylthio, 1-naphthylthio, 2-naphthylthio, preferably methylthio, ethylthio and phenylthio;

C$_1$–C$_{12}$-alkoxy groups, preferably C$_1$–C$_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

C$_6$–C$_{14}$-aryloxy groups such as phenoxy, 1-naphthoxy, 2-naphthoxy, 1-anthroxy, 2-anthroxy and 9-anthroxy, preferably phenoxy, 1-naphthoxy and 2-naphthoxy, particularly preferably phenoxy, C$_1$–C$_{12}$-thioether groups such as methylthio, ethylthio, propylthio, 1-methylpropylthio, 1,1-dimethylethylthio, phenylthio, 1-naphthylthio, 2-naphthylthio, preferably methylthio, ethylthio and phenylthio;

silyloxy groups OSiR$^7$R$^8$R$^9$, where R$^7$ to R$^9$ are selected independently from among hydrogen, C$_1$–C$_6$-alkyl groups, benzyl radicals and C$_6$–C$_{14}$-aryl groups; preference is given to the trimethylsilyloxy, triethylsilyloxy, triisopropylsilyloxy, diethylisopropylsilyloxy, dimethylthexlsilyloxy, tert-butyldimethylsilyloxy, tert-butyldiphenylsilyloxy, tribenzylsilyloxy, triphenylsilyloxy and tri-para-xylylsilyloxy groups; particular preference is given to the trimethylsilyloxy group and the tert-butyldimethylsilyloxy group;

halogens such as fluorine, chlorine, bromine and iodine, with preference being given to fluorine and chlorine;

or amino groups NR$^{10}$R$^{11}$, where R$^{10}$ and R$^{11}$ are selected independently from among hydrogen, C$_1$–C$_6$-alkyl groups and C$_6$–C$_{14}$-aryl groups, which may form a saturated or unsaturated 5–10-membered ring; preference is given to the dimethylamino, diethylamino, diisopropylamino, methylphenylamino and diphenylamino groups. Examples of amino groups having saturated rings are the N-piperidyl group and the N-pyrrolidinyl group; examples of amino groups having unsaturated rings are the N-pyrryl, N-indolyl and N-carbazolyl groups.

R$^1$ and R$^2$ may be joined to one another and, together with the carbon atoms of the parent aromatic, form a 5- to 8-membered ring. For example, R$^1$ and R$^2$ can together be: —(CH$_2$)$_3$—(trimethylene), —(CH$_2$)$_4$—(tetramethylene), —(CH$_2$)$_5$—(pentamethylene), —(CH$_2$)$_6$—(hexamethylene), —CH$_2$—CH=CH—, —CH$_2$—CH=CH—CH$_2$—, —CH=CH—CH=CH—, —O—CH$_2$—O—, —O—CH(CH$_3$)—O—, —CH—(C$_6$H$_5$)—O—, —O—CH$_2$—CH$_2$—O—, —O—C(CH$_3$)$_2$—O—, —N(CH$_3$)—CH$_2$—CH$_2$—N(CH$_3$)—, —N(CH$_3$)—CH$_2$—N(CH$_3$)— or —O—Si(CH$_3$)$_2$—O—.

R$^3$ is selected from among the following groups:

α-branched C$_3$–C$_{12}$-alkyl such as isopropyl, isobutyl, tert-butyl, 2-pentyl, 3-pentyl, 2-hexyl, 3-hexyl, 2-isopentyl, 3-isopentyl, neopentyl, 1,2-dimethylpropyl, 2-heptyl, 3-heptyl, 2-isoheptyl, 3-isoheptyl, 2-octyl, 3-octyl, 2-nonyl, 3-nonyl, 4-nonyl, 1-decyl, 2-decyl, 3-decyl, 4-decyl, 2-undecyl, 3-undecyl, 4-undecyl, 5-undecyl, 2-dodecyl, 3-dodecyl, 4-dodecyl, 5-dodecyl, preferably α-branched C$_1$–C$_6$-alkyl groups such as isopropyl, isobutyl, tert-butyl, 2-pentyl, 3-pentyl, 2-hexyl, 3-hexyl, 2-isopentyl, neopentyl, 1,2-dimethylpropyl and 3-isopentyl, particularly preferably isopropyl, isobutyl and tert-butyl;

C$_3$–C$_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

examples of substituted cycloalkyl groups are: 2-methylcyclopentyl, 3-methylcyclopentyl, cis-2,4-dimethylcyclopentyl, trans-2,4-dimethylcyclopentyl 2,2,4,4-tetramethylcyclopentyl, 2-methylcyclohexyl, 3-methylcyclohexyl, 4-methylcyclohexyl, cis-2,5-dimethylcyclohexyl, trans-2,5-dimethylcyclohexyl, 2,2,5,5-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,5,5-tetrachlorocyclohexyl, 2-thiomethylcyclopentyl, 2-thiomethylcyclohexyl, 3-thiomethylcyclopentyl or 3-thiomethylcyclohexyl;

C$_7$–C$_{20}$-aralkyl, preferably C$_7$–C$_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

C$_2$–C$_{10}$-alkenyl having at least one double bond conjugated with the aromatic, preferably vinyl, prop-1-enyl, but-1-enyl, isobutenyl, buta-1,3-dienyl, pent-1-enyl, isoprenyl, hex-1-enyl, oct-1-enyl or dec-1-enyl; particularly preferably vinyl, prop-1-enyl, isobutenyl and buta-1,3-dienyl;

C$_6$–C$_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

C$_6$–C$_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl substituted by one or more C$_1$–C$_{12}$-alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl, and n-dodecyl; preferably C$_1$–C$_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably C$_1$–C$_4$-alkyl such as methyl, ethyl, n-propyl, isopropyl, n-butyl, isobutyl, sec-butyl and tert-butyl;

halogens such as fluorine, chlorine, bromine and iodine, with preference being given to fluorine and chlorine, monohalogenated or polyhalogenated C$_1$–C$_{12}$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

C$_1$–C$_{12}$-alkoxy groups, preferably C$_1$–C$_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

silyloxy groups OSiR$^7$R$^8$R$^9$ where R$^7$ to R$^9$ are selected independently from among hydrogen, C$_1$–C$_6$-alkyl groups, benzyl radicals and C$_6$–C$_{14}$-aryl groups; preference is given to the trimethylsilyloxy, triethylsilyloxy, triisopropylsilyloxy, diethylisopropylsilyloxy, dimethylthexlsilyloxy, tert-butyldimethylsilyloxy, tert-butyldiphenylsilyloxy, tribenzylsilyloxy, triphenylsilyloxy and tri-para-xylylsilyloxy groups; particular preference is given to the trimethylsilyloxy group and the tert-butyldimethylsilyloxy group;

or amino groups $NR^{10}R^{11}$, where $R^{10}$ and $R^{11}$ are selected independently from among hydrogen, $C_1$–$C_6$-alkyl groups, benzyl radicals and $C_6$–$C_{14}$-aryl groups, which may form a saturated or unsaturated 5–10-membered ring; preference is given to the dimethylamino, diethylamino, diisopropylamino, methylphenylamino and diphenylamino groups. Examples of amino groups having saturated rings are the N-piperidyl group and the N-pyrrolidinyl group; examples of amino groups having unsaturated rings are the N-pyrryl, N-indolyl and N-carbazolyl groups;

$C_1$–$C_{12}$-alkoxy groups, preferably $C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, 1-naphthoxy, 2-naphthoxy, 1-anthroxy, 2-anthroxy and 9-anthroxy, preferably phenoxy, 1-naphthoxy and 2-naphthoxy, particularly preferably phenoxy, $C_1$–$C_{12}$-thioether groups such as methylthio, ethylthio, propylthio, 1-methylpropylthio, 1,1-dimethylethylthio, phenylthio, 1-naphthylthio, 2-naphthylthio, preferably methylthio, ethylthio and phenylthio;

silyloxy groups $OSiR^7R^8R^9$, where $R^7$ to $R^9$ are selected independently from among hydrogen, $C_1$–$C_6$-alkyl groups, benzyl groups and $C_6$–$C_{14}$-aryl groups; preference is given to the trimethylsilyloxy, triethylsilyloxy, triisopropylsilyloxy, diethylisopropylsilyloxy, dimethylhexylsilyloxy, tert-butyldimethylsilyloxy, tert-butyldiphenylsilyloxy, tribenzylsilyloxy, triphenylsilyloxy and tri-para-xylylsilyloxy groups; particular preference is given to the trimethylsilyloxy group and the tert-butyldimethylsilyloxy group;

halogens such as fluorine, chlorine, bromine and iodine, with preference being given to fluorine and chlorine;

or amino groups $NR^{10}R^{11}$, where $R^{10}$ and $R^{11}$ are selected independently from among hydrogen, $C_1$–$C_6$-alkyl groups, benzyl groups and $C_6$–$C_{14}$-aryl groups, which may form a saturated or unsaturated 5–10-membered ring; particular preference is given to the dimethylamino, diethylamino, diisopropylamino, methylphenylamino and diphenylamino groups. Examples of amino groups having saturated rings are the N-piperidyl group and the N-pyrrolidinyl group; examples of amino groups having unsaturated rings are the N-pyrryl, N-indolyl and N-carbazolyl groups.

In a preferred embodiment, $R^3$ together with an adjacent radical, i.e. $R^2$ or $R^4$, forms a 5- to 8-membered ring which may bear further substituents. For example, $R^3$ and $R^2$ or $R^4$ can together be: —(CH$_2$)$_3$—(trimethylene), —(CH$_2$)$_4$—(tetramethylene), —(CH$_2$)$_5$—(pentamethylene), —(CH$_2$)$_6$—(hexamethylene), —CH$_2$—CH=CH—, —CH$_2$—CH=CH—CH$_2$—, —CH=CH—CH=CH—, —O—CH$_2$—O—, —O—CH(CH$_3$)—O—, —CH—(C$_6$H$_5$)—O—, —O—CH$_2$—CH$_2$—O—, —O—C(CH$_3$)$_2$—O—, —N(CH$_3$)—CH$_2$—CH$_2$—N(CH$_3$)—, —N(CH$_3$)—CH$_2$—N(CH$_3$)— or —O—Si(CH$_3$)$_2$—O—.

In a particularly preferred embodiment, $R^3$ and $R^4$ together form a system as in the formula Ia.

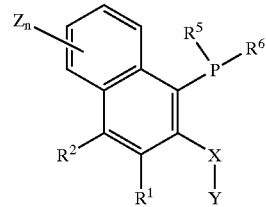

Ia

In this formula, the gruops Z are identical or different and selected from among the following groups:

hydrogen, halogen such as fluorine, chlorine, bromine and iodine, preferably fluorine or chlorine;

$C_1$–$C_4$-alkyl such as methyl, ethyl, n-propyl, isopropyl, n-butyl, isobutyl, sec-butyl and tert-butyl;

$C_1$–$C_4$-alkoxy such as methoxy, ethoxy, n-propoxy, n-butoxy and tert-butoxy, and n is an integer from 0 to 4.

$R^5$ and $R^6$ are selected independently from among the following groups:

α-branched $C_3$–$C_{12}$-alkyl such as isopropyl, isobutyl, tert-butyl, 2-pentyl, 3-pentyl, 2-hexyl, 3-hexyl, 2-isopentyl, 3-isopentyl, neopentyl, 1,2-dimethylpropyl, 2-heptyl, 3-heptyl, 2-isoheptyl, 3-isoheptyl, 2-octyl, 3-octyl, 2-nonyl, 3-nonyl, 4-nonyl, 1-decyl, 2-decyl, 3-decyl, 4-decyl, 2-undecyl, 3-undecyl, 4-undecyl, 5-undecyl, 2-dodecyl, 3-dodecyl, 4-dodecyl, 5-dodecyl, preferably α-branched $C_1$–$C_6$-alkyl groups such as isopropyl, isobutyl, tert-butyl, 2-pentyl, 3-pentyl, 2-hexyl, 3-hexyl, 2-isopentyl, neopentyl, 1,2-dimethylpropyl and 3-isopentyl, particularly preferably the isopropyl group;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

examples of substituted cycloalkyl groups are: 2-methylcyclopentyl, 3-methylcyclopentyl, cis-2,4-dimethylcyclopentyl, trans-2,4-dimethylcyclopentyl, 2,2,4,4-tetramethylcyclopentyl, 2-methylcyclohexyl, 3-methylcyclohexyl, 4-methylcyclohexyl, cis-2,5-dimethylcyclohexyl, trans-2,5-dimethylcyclohexyl, 2,2,5,5-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,5,5-tetrachlorocyclohexyl, 2-thiomethylcyclopentyl, 2-thiomethylcyclohexyl, 3-thiomethylcyclopentyl, 3-thiomethylcyclohexyl and further derivatives.

X is oxygen, sulfur, selenium, N—$R^{12}$, P—$R^{12}$ or As$R^{12}$. Here, $R^{12}$ is selected from among hydrogen, $C_1$–$C_6$-alkyl groups, benzyl groups and $C_6$–$C_{14}$-aryl groups.

Y is:

hydrogen, an alkali metal cation such as $Li^+$, $Na^+$, $K^+$, $Rb^+$ and $Cs^+$, preferably $Na^+$ and $K^+$;

a C$_1$–C$_{18}$-alkylacyl anion such as acetate, propionate, n-butyrate, isobutyrate, valerate, capronate, decanoate and stearate; preference is given to the C$_1$–C$_6$-alkylacyl anions acetate, propionate, n-butyrate and isobutyrate, particularly preferably acetate;

a C$_6$–C$_{14}$-arylacyl anion, preferably benzoate, α-naphthoate, β-naphthoate or 9-anthracenecarboxylate, particularly preferably benzoate;

SiR$^7$R$^8$R$^9$, where R$^7$ to R$^9$ are selected independently from among hydrogen, C$_1$–C$_6$-alkyl groups, benzyl groups and C$_6$–C$_{14}$-aryl groups; preference is given to the trimethylsilyloxy, triethylsilyloxy, triisopropylsilyloxy, diethylisopropylsilyloxy, dimethylthexlsilyloxy, tert-butyldimethylsilyloxy, tert-butyldiphenylsilyloxy, tribenzylsilyloxy, triphenylsilyloxy and tri-para-xylylsilyloxy groups; particular preference is given to the trimethylsilyloxy group and the tert-butyldimethylsilyloxy group.

The synthesis of the ligands can be carried out by methods known per se. A suitable method is described by J. Heinicke, U. Jux, R. Kadyrov and M. He in Heteroatomic Chem. 1997, 8, 383–396, specifically page 393, and by J. Heinicke, M. He, R. Kadyrov, P. G. Jones in Heteroatomic Chem. 1998, 9, 183–193. Further methods are described in T. Rauchfuβ, Inorg. Chem. 1977, 16, 2966. Specific ortho-dialkylphosphinocresol syntheses are published in J. Heinicke et al., J. Organomet. Chem. 1983, 243, 1, J. Heinicke et al. Chem. Ber. 1996, 129, 1061 and Chem. Ber. 1996, 129, 1547.

The preparation of the complexes from the metal precursor and ligand is advantageously carried out immediately prior to the polymerization.

To prepare the complexes, the ligand of the formula I is mixed with the metal precursor, preferably in a solvent. Suitable solvents are toluene, ethylbenzene, chlorobenzene, dichlorobenzene, ortho-xylene, meta-xylene, para-xylene and mixtures thereof. Furthermore, cyclic ethers such as tetrahydrofuran, dioxane or acyclic ethers such as diethyl ether, di-n-butyl ether, diisopropyl ether or 1,2-dimethoxyethane are also suitable. Further suitable solvents are ketones such as acetone, methyl ethyl ketone or diisobutyl ketone, likewise amides such as dimethylformamide or dimethylacetamide. Mixtures of these solvents with one another are also suitable.

Appropriate molar ratios of ligand to metal compound are in the range from 2:1 to 1:5. The range from 1.1:1 to 1:1.1 is preferred.

It is assumed that the complexes of the present invention are predominantly present as chelate structures as in formula II or IIa or else are in dimeric or oligomerized form.

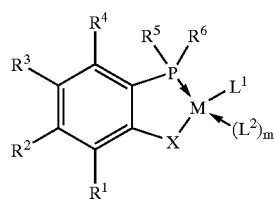

II

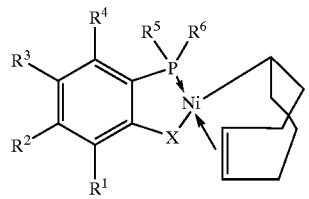

IIa

In these formulae, the radicals R$^1$–R$^6$ and also M and X are as defined above; m is selected from among the integers 1, 2 and 3.

The ligand L$^1$ can be hydrogen or one of the following radicals:

C$_1$–C$_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl, and n-dodecyl; preferably C$_1$–C$_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably C$_1$–C$_4$-alkyl such as methyl, ethyl, n-propyl, isopropyl, n-butyl, isobutyl, sec-butyl and tert-butyl;

C$_3$–C$_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl;

examples of substituted cycloalkyl groups are: 2-methylcyclopentyl, 3-methylcyclopentyl, cis-2,4-dimethylcyclopentyl, trans-2,4-dimethylcyclopentyl, 2,2,4,4-tetramethylcyclopentyl, 2-methylcyclohexyl, 3-methylcyclohexyl, 4-methylcyclohexyl, cis-2,5-dimethylcyclohexyl, trans-2,5-dimethylcyclohexyl, 2,2,5,5-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,5,5-tetrachlorocyclohexyl, 2-thiomethylcyclopentyl, 2-thiomethylcyclohexyl, 3-thiomethylcyclopentyl, 3-thiomethylcyclohexyl and further derivatives.

As ligand L$^2$, use is made of the customary uncharged molecules or anions used in coordination chemistry (cf. Elschenbroich, Salzer, "Einführung in die Organometallchemie", 3$^{rd}$ Edition, B. G. Teubner Verlag, Stuttgart 1990). Examples of suitable ligands are:

aliphatic and aromatic phosphines R$_x$PH$_{3-x}$, amines R$_x$NH$_{3-x}$, where R is selected from among the radicals defined under R$^1$ to R$^4$,

CO, nitriles containing C$_1$–C$_{12}$-alkyl or C$_6$–C$_{14}$-aryl radicals, for example acetonitrile, propionitrile, butyronitrile or benzonitrile, halide ions such as fluoride, chloride, bromide or iodide, allyl anions, benzyl anions, aryl anions such as the phenyl anion, C$_1$–C$_6$-alkyl anions such as (CH$_3$)—, (C$_2$H$_5$)—, (C$_3$H$_7$)—, (n-C$_4$H$_9$)—, (tert-C$_4$H$_9$)— or (C$_6$H$_{14}$)—;

singly or multiply ethylenically unsaturated double bond systems such as ethenyl, propenyl, cis-2-butenyl, trans-2-butenyl, cyclohexenyl, norbornenyl, 1,5-cyclooctadienyl ligands ("COD"), 1,6-cyclodecadienyl ligands, 1,5,9-all-trans-cyclododecatrienyl ligands or norbornadienyl ligands.

In a particularly preferred embodiment, the ligands $L^1$ and $L^2$ are linked to one another via one or more covalent bonds. Examples of such ligands are the 4-cyclooctenyl ligand, the 5-cyclodecenyl ligand and the all-trans-1,4-cyclododecadienyl ligand.

The polymerization of 1-olefins using the metal complexes of the present invention can be carried out in a manner known per se.

Here, the order of addition of the reagents in the polymerization is not critical. Thus, gaseous monomer can firstly be injected onto the solvent or liquid monomer can firstly be metered in, followed by addition of the catalyst. However, it is also possible firstly to dilute the catalyst solution with further solvent and subsequently to add monomer.

Examples of 1-olefins which are suitable for the polymerization are: ethylene, propylene, 1-butene, 1-pentene, 1-hexene, 1-heptene, 1-octene, 1-decene and 1-eicosene, and also branched olefins such as 4-methyl-1-pentene, vinylcyclohexene and vinylcyclohexane as well as styrene, para-methylstyrene and para-vinylpyridine, with preference being given to ethylene and propylene. Particular preference is given to ethylene.

The copolymerization of two 1-olefins can also be carried out using the catalyst system of the present invention, with the comonomer being able to be selected from the following groups:

1-Olefins such as ethylene, propylene, 1-butene, 1-pentene, 1-hexene, 1-heptene, 1-octene, 1-decene and 1-eicosene, and also branched olefins such as 4-methyl-1-pentene, vinylcyclohexene and vinylcyclohexane as well as styrene, para-methylstyrene and para-vinylpyridine, with preference being given to propylene, 1-butene, 1-pentene, 1-hexene, 1-heptene, 1-octene, 1-decene;

polar monomers such as acrylic acid, $C_1$–$C_6$-alkyl acrylates, methacrylic acid, $C_1$–$C_6$-alkyl methacrylates, $C_1$–$C_6$-alkyl vinyl ethers and vinyl acetate; preference is given to methyl acrylate, ethyl acrylate, n-butyl acrylate, methyl methacrylate, ethyl methacrylate, butyl methacrylate, ethyl vinyl ether and vinyl acetate.

Here, the ratio of the two monomers can be chosen without restriction.

The actual polymerization usually proceeds at a pressure of 1–4000 bar and temperatures of 10–250° C., with preference being given to the ranges 2–100 bar and 40–150° C.

Suitable solvents are aromatic solvents such as benzene, toluene, ethylbenzene, chlorobenzene, dichlorobenzene, ortho-xylene, meta-xylene and para-xylene and also mixtures thereof. Further suitable solvents are cyclic ethers such as tetrahydrofuran, dioxane or acyclic ethers such as diethyl ether, di-n-butyl ether, diisopropyl ether or 1,2-dimethoxyethane. Also suitable are ketones such as acetone, methyl ethyl ketone or diisobutyl ketone, likewise amides such as dimethylformamide or dimethylacetamide. Furthermore, mixtures of these solvents with one another as well as mixtures of these solvents with water or alcohols such as methanol or ethanol are also suitable.

Modern industrial polymerization processes for olefins are suspension processes, bulk polymerization processes in the liquid or supercritical monomer and also gas-phase processes. The latter may be stirred gas phase or fluidized-bed gas-phase processes.

In these industrial processes, it is advantageous for catalytically active substances to be immobilized on a solid support. Otherwise, morphology problems with the polymer (lumps, wall deposits, blockages in lines or heat exchangers) can result, forcing shutdown of the plant.

The catalyst system of the present invention can readily be deposited on a solid support without suffering any significant drop in activity. Suitable support materials are, for example, porous metal oxides of metals of groups 2–14, for example Mg, Ca, Sr, Ba, B, Al, Ti, Zr, Fe, Zn or Si or else mixtures thereof, also sheet silicates as well as solid halides such as fluorides, chlorides or bromides of metals of groups 1, 2 and 13, e.g. Na, K, Mg, Ca or Al. Preferred examples of metal oxides of groups 2–14 are $SiO_2$, $B_2O_3$, $Al_2O_3$, MgO, CaO and ZnO. Preferred sheet silicates are montmorillonites or bentonites; preferred halides are $MgCl_2$ and amorphous $AlF_3$.

Particularly preferred support materials are spherical silica gels and aluminosilicate gels of the formula $SiO_2 \cdot a\, Al_2O_3$, where a is generally a number in the range from 0 to 2, preferably from 0 to 0.5. Such silica gels are commercially available, e.g. Silica Gel 332 or S 2101 from W.R. Grace.

As particle size of the support material, it has been found to be useful to employ mean particle diameters in the range 1–300 μm, preferably from 20 to 80 μm, with the particle diameter being determined by known methods such as sieving. The pore volume of these supports is generally from 1.0 to 3.0 ml/g, preferably from 1.6 to 2.2 ml/g and particularly preferably from 1.7 to 1.9 ml/g. The BET surface area is 200–750 $m^2$/g, preferably 250–400 $m^2$/g.

To remove impurities, in particular moisture, adhering to the support material, the support materials can be baked out prior to doping. Temperatures of 45–1000° C. are suitable for this purpose. Temperatures of 100–750° C. are particularly useful for silica gels and other metal oxides; for $MgCl_2$ supports, the temperature range 50–100° C. is preferred. This baking-out should be carried out for a period of from 0.5 to 24 hours, preferably from 1 to 12 hours. The pressure conditions are not critical per se; the baking-out can be carried out at atmospheric pressure. However, reduced pressures of from 0.1 to 500 mbar are advantageous; a range from 1 to 100 mbar is particularly advantageous and a range from 2 to 20 mbar is very particularly advantageous. Chemical pretreatment of the support material is also possible.

However, the metal complex system of the present invention is generally so insensitive toward impurities that the preliminary heating of the support material can be omitted.

The doping of the catalyst is generally carried out by slurrying the support material in a suspension medium and combining the suspension with the solution of the metal complex system. Here, the volume of the suspension medium is generally from 1 to 20 times the pore volume of the catalyst support.

The low water-sensitivity of the metal complex system of the present invention also allows it to be used in emulsion polymerizations. As emulsifiers, it is possible to use anionic, cationic and also nonionic emulsifiers.

Useful nonionic emulsifiers are, for example, ethoxylated monoalkylphenols, dialkylphenols and trialkylphenols (EO content: 3–50, alkyl radical: $C_4$–$C_{12}$) and ethoxylated fatty alcohols (EO content: 3–80; alkyl radical: $C_8$–$C_{36}$). Examples are the Lutensol® products from BASF AG.

Customary anionic emulsifiers are, for example, alkali metal and ammonium salts of alkyl sulfates (alkyl radical: $C_8$–$C_{12}$), of sulfuric monoesters of ethoxylated alkanols (EO content: 4–30, alkyl radical: $C_{12}$–$C_{18}$) and ethoxylated alkylphenols (EO content: 3–50, alkyl radical: $C_4$–$C_{12}$), of alkylsulfonic acids (alkyl radical: $C_{12}$–$C_{18}$) and of alkylarylsulfonic acids (alkyl radical: $C_8$–$C_{18}$).

Suitable cationic emulsifiers are, in general, primary, secondary, tertiary or quaternary ammonium salts containing a $C_6$–$C_{18}$-alkyl, $C_6$–$C_{18}$-aralkyl or heterocyclic radical, alkanolammonium salts, pyridinium salts, imidazolinium salts, oxazolinium salts, morpholinium salts, thiazolinium salts and also salts of amine oxides, quinolinium salts, isoquinolinium salts, tropylium salts, sulfonium salts and phosphonium salts. Examples which may be mentioned are dodecylammonium acetate or the corresponding hydrochloride, the chlorides or acetates of the various 2-(N,N,N-trimethylammonium)ethylparaffinic acid esters, N-cetylpyridinium chloride, N-laurylpyridinium sulfate and also N-cetyl-N,N,N-trimethylammonium bromide, N-dodecyl-N,N,N-trimethylammonium bromide, N,N-distearyl-N,N-dimethylammonium chloride and also the Gemini surfactant N,N'-(lauryldimethyl)ethylenediamine dibromide. Numerous further examples may be found in H. Stache, Tensid-Taschenbuch, Carl-Hanser-Verlag, Munich, Vienna, 1981 and in McCutcheon's, Emulsifiers & Detergents, MC Publishing Company, Glen Rock, 1989.

The solid polymers obtained generally have molecular weights of over 10,000.

The molding compositions obtained from the polymers are well suited to conversion into films, sheets, waxes or hollow bodies such as bottles, etc. For this purpose, they can be processed by customary methods such as extrusion, injection molding or pressing and sintering. Wax-like materials can, for example, be processed by pelletization or extrusion and can be used in typical wax applications.

WORKING EXAMPLES

General Procedure

The indicated amounts of ligand and Ni(COD)$_2$ were each dissolved at 0° C. in 10 ml of the solvent kept under an argon atmosphere. The two solutions were subsequently mixed, stirred for 10 minutes at 0° C. and a further 30 minutes at room temperature and subsequently transferred to an autoclave which had been made inert by means of argon. While stirring, ethylene was injected until the indicated pressure had been reached and the temperature was set to that given in Table 1. Polymerization was carried out for 15 hours as indicated in Table 1, and the autoclave was then vented via a cold trap cooled to −60° C. and the volatile constituents were removed by flash distillation at 25–30° C./10$^{-2}$ mbar. Catalyst residues were subsequently removed by treatment with methanolic hydrochloric acid, the polymer was washed with methanol and dried to constant weight at 25–30° C./10$^{-2}$ bar.

All experiments were repeated at least once; in the case of slight variation of the results, the average was calculated.

Ligands 4,6-Di-tert-butyl-2-(diisopropylphosphino)phenol (formula 1)

4,6-Di-tert-butyl-2-(dicyclohexylphosphino)phenol (formula 2)

4-Methoxy-2-dicyclohexylphosphinophenol (formula 3)

4-Fluoro-2-diisopropylphosphinophenol (formula 4)

Example 1

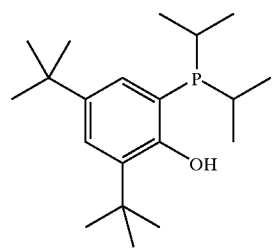

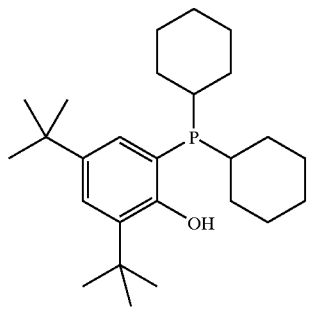

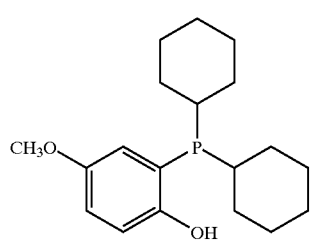

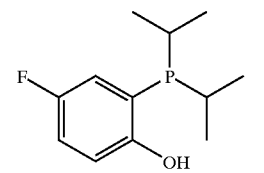

This example was carried out using 41.8 mg (0.12 mmol) of 4,6-di-tert-butyl-2-(diisopropylphosphino)phenol (formula 1) as ligand and 35.5 mg (0.12 mmol) of Ni(COD)$_2$. As solvent for the complexation, 20 ml of toluene were used. Polymerization was carried out for 15 hours at 80° C. and a pressure of 50 bar. The yield of polymer and analytical data for the polymer are shown in Table 1.

Example 2

This example was carried out using 40.3 mg (0.1 mmol) of 4,6-di-tert-butyl-2-(dicyclohexylphosphino)phenol (formula 2) as ligand and 27.4 mg (0.1 mmol) of Ni(COD)$_2$. As solvent for the complexation, 20 ml of toluene were used. Polymerization was carried out for 15 hours at 100° C. and a pressure of 50 bar. The yield of polymer and analytical data for the polymer are shown in Table 1.

Example 3

This example was carried out using 32.0 mg (0.1 mmol) of 4-methoxy-2-dicyclohexylphosphinophenol (formula 3) as ligand and 27.5 mg (0.1 mmol) of Ni(COD)$_2$. As solvent for the complexation, 20 ml of toluene were used. Polymerization was carried out for 15 hours at 100° C. and a pressure of 50 bar. The yield of polymer and analytical data for the polymer are shown in Table 1.

Example 4

This example was carried out using 22.8 mg (0.1 mmol) of 4-fluoro-2-diisopropylphosphinophenol (formula 4) as ligand and 27.4 mg (0.1 mmol) of Ni(COD)$_2$. As solvent for the complexation, 20 ml of toluene were used. Polymerization was carried out for 15 hours at 100° C. and a pressure of 50 bar. The yield of polymer and analytical data for the polymer are shown in Table 1.

COMPARATIVE EXAMPLES

Ligands for the Comparative Examples ortho-Diethylphosphinophenol (formula A' from U.S. Pat. No. 4,472,525) 4-Methyl-2-(phenylisopropylphosphino)phenol (formula C from U. Jux, Thesis, University of Greifswald, 1996)

4-Methyl-2-(phenylisopropylphosphino)phenyl trimethylsilyl ether (formula C' from U. Jux, Thesis, University of Greifswald, 1996) ortho-Diphenylphosphinophenol (formula C" from U. Jux, Thesis, University of Greifswald, 1996)

4-Methyl-2-diphenylphosphinophenol (formula D, this and the following examples from Poster of M. He, J. Heinicke et al., GDCh Conference, Munich, Poster B197, Aug. 20, 1998)

4-Methoxy-2-diphenylphosphinophenol (formula D')

4,6-Di-tert-butyl-2-diphenylphosphinophenol (formula D")

4,6-Di-tert-butyl-2-(phenyl-tert-butylphosphino)phenol (formula

4-Methyl-2-(phenyl-tert-butylphosphino)phenol (formula D"")

Comparative Example C1

0.55 g (2 mmol) of Ni(COD)$_2$ in 30 ml of benzene were admixed with 364 mg (2 mmol) of ortho-diethylphosphinophenol (formula A') and the mixture was transferred to an autoclave containing an inert gas atmosphere. Ethylene was injected and the autoclave was heated while stirring until a temperature of 70–80° C. had been reached. Polymerization was subsequently carried out for 16 hours. In the work-up, only small amounts of oligomers, but no polyethylene, were found.

Comparative Example C2

This experiment was carried out using 56.8 mg (0.22 mmol) of 4-methyl-2-(phenylisopropylphosphino)phenol (formula C) as ligand and 60.5 mg (0.22 mmol) of Ni(COD)$_2$. As solvent for the complexation, 20 ml of toluene were used. Polymerization was carried out for 12 hours at 120° C. and a pressure of 40 bar. The yield of polymer and analytical data for the polymer are shown in Table 1.

Comparative Example C3

This experiment was carried out using 72.6 mg (0.22 mmol) of 4-methyl-2-(phenylisopropylphosphino)phenyl trimethylsilyl ether (formula C') as ligand and 60.5 mg (0.22 mmol) of Ni(COD)$_2$. As solvent for the complexation, 20 ml of toluene were used. Polymerization was carried out for 12 hours at 120° C. and a pressure of 40 bar. The yield of polymer and analytical data for the polymer are shown in Table 1.

Comparative Example C4

This experiment was carried out using 55.6 mg (0.22 mmol) of 2-diphenylphosphinophenol (formula C") as ligand and 55 mg (0.2 mmol) of Ni(COD)$_2$. As solvent for the complexation, 30 ml of toluene were used. Polymerization was carried out for 15 hours at 100° C. and a pressure of 50 bar. The yield of polymer and analytical data for the polymer are shown in Table 1.

Comparative Example C5

This experiment was carried out using 29.2 mg (0.1 mmol) of 4-methyl-2-diphenylphosphinophenol (formula D) as ligand and 27.4 mg (0.1 mmol) of Ni(COD)$_2$. As solvent for the complexation, 20 ml of toluene were used. Polymerization was carried out for 15 hours at 100° C. and a pressure of 50 bar. The yield of polymer and analytical data for the polymer are shown in Table 1.

Comparative Example C6

This experiment was carried out using 30.8 mg (0.1 mmol) of 4-methoxy-2-diphenylphosphinophenol (formula D') as ligand and 27.4 mg (0.1 mmol) of Ni(COD)$_2$. As solvent for the complexation, 20 ml of toluene were used. Polymerization was carried out for 15 hours at 100° C. and a pressure of 50 bar. The yield of polymer and analytical data for the polymer are shown in Table 1.

Comparative Example C7

This experiment was carried out using 39.0 mg (0.1 mmol) of 4,6-di-tert-butyl-2-diphenylphosphinophenol (formula D") as ligand and 27.5 mg (0.1 mmol) of Ni(COD)$_2$. As solvent for the complexation, 20 ml of toluene were used. Polymerization was carried out for 15 hours at 100° C and a pressure of 50 bar. The yield of polymer and analytical data for the polymer are shown in Table 1.

Comparative Example C8

This experiment was carried out using 37.1 mg (0.1 mmol) of 4,6-di-tert-butyl-2-(phenyl-tert-butylphosphino)phenol (formula D''') as ligand and 27.5 mg (0.1 mmol) of Ni(COD)$_2$. As solvent for the complexation, 20 ml of toluene were used. Polymerization was carried out for 15 hours at 100° C. and a pressure of 50 bar. The yield of polymer and analytical data for the polymer are shown in Table 1.

Comparative Example C9

This experiment was carried out using 27.2 mg (0.1 mmol) of 4-methyl-2-(phenyl-tert-butylphosphino)phenol (formula D"") as ligand and 27.5 mg (0.1 mmol) of Ni(COD)$_2$. As solvent for the complexation, 20 ml of toluene were used. Polymerization was carried out for 15 hours at 100° C. and a pressure of 50 bar. The yield of polymer and analytical data for the polymer are shown in Table 1.

TABLE 1

Polymerization results for Examples 1 to 4 and Comparative Examples C1–C9

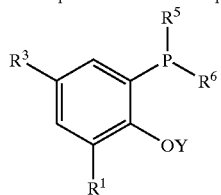

| Ligand | $R^1$ | $R^3$ | $R^5$ | $R^6$ | Y | T [° C.] | g of polymer | g of oligomers | Conversion | kg PE/mol Ni · h | M.p./° C. | $M_{w/g}$ |
|---|---|---|---|---|---|---|---|---|---|---|---|---|
| 1 | t-Bu | t-Bu | i-Pr | i-Pr | H | 80 | 8.0 | — | 54% | 4.4 | 120.6 | 23,230 |
| 2 | t-Bu | t-Bu | Cy | Cy | H | 100 | 8.3 | <<0.1 | 93.3% | 5.5 | 111–114 | 12,600 |
| 3 | H | OMe | Cy | Cy | H | 100 | 8.5 | 0.3 | 63.8% | 5.7 | 128–130 | 14,768 |
| 4 | H | F | i-Pr | i-Pr | H | 100 | 11.8 | 0.4 | 79.2% | 7.6 | 125–128 | 24,690 |
| A' (C1) | H | H | Et | Et | H | 55–75 | — | 0.2 | 3.5% | 0 | — | — |
| C (C2) | H | Me | Ph | i-Pr | H | 120 | 3.6 | — | 41% | 1.4 | n.d. | n.d. |
| C' (C3) | H | OMe | Ph | i-Pr | SiMe$_3$ | 120 | 3.6 | 0.6 | 48% | 1.4 | 121 | 9310 |
| C" (C4) | H | H | Ph | Ph | H | 100 | 6.4 | 0.2 | 53% | 2.1 | 117–123 | 5510 |
| D (C5) | H | Me | Ph | Ph | H | 100 | 9.2 | 0.3 | 78% | 6.1 | 116–123 | 5600 |
| D' (C6) | H | OMe | Ph | Ph | H | 100 | 12.8 | 0.4 | 89% | 8.5 | 115–118 | 4600 |
| D" (C7) | t-Bu | t-Bu | Ph | Ph | H | 100 | 6.5 | 0.1 | 56% | 4.3 | 119–125 | 8110 |
| D'" (C8) | t-Bu | t-Bu | t-Bu | Ph | H | 100 | 14.4 | 0.2 | 96% | 9.6 | 120–126 | 5682 |
| D"" (C9) | H | Me | t-Bu | Ph | H | 100 | 11.9 | 0.2 | 88% | 7.9 | 114–117 | 5807 |

Abbreviations for the radicals: Me = methyl, Et = ethyl, i-Pr = isopropyl, t-Bu = tert-butyl; Cy = cyclohexyl, Ph = phenyl, OMe = methoxy, SiMe$_3$ = trimethylsilyl.

We claim:

1. A metal complex obtainable from a metal precursor of a metal of the $6^{th}$–$10^{th}$ groups of the Periodic Table in the oxidation state 0 or +2 and a ligand of the formula I,

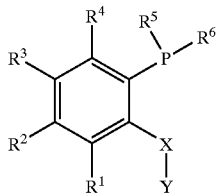

where $R^1$, $R^2$ and $R^4$ are, independently of one another:
hydrogen,
$C_1$–$C_{12}$-alkyl,
$C_1$–$C_{12}$-alkyl bearing one or more identical or different $C_1$–$C_{12}$-alkyl groups, halogens, $C_1$–$C_{12}$-alkoxy groups or $C_1$–$C_{12}$-thioether groups as substituents,
$C_7$–$C_{20}$-arylalkyl,
$C_2$–$C_{12}$-alkenyl,
$C_3$–$C_{12}$-cycloalkyl,
$C_3$–$C_{12}$-cycloalkyl bearing one or more identical or different $C_1$–$C_{12}$-alkyl groups, halogens, $C_1$–$C_{12}$-alkoxy groups or $C_1$–$C_{12}$-thioether groups as substituents,
$C_6$–$C_{14}$-aryl,
$C_6$–$C_{14}$-aryl bearing one or more identical or different $C_1$–$C_{12}$-alkyl groups, halogens, monohalogenated or polyhalogenated $C_1$–$C_{12}$-alkyl groups, $C_1$–$C_{12}$-alkoxy groups, silyloxy groups $OSiR^7R^8R^9$, amino groups $NR^{10}R^{11}$ or $C_1$–$C_{12}$-thioether groups as substituents,
$C_1$–$C_{12}$-alkoxy groups,
$C_6$–$C_{14}$-aryloxy groups,
$C_1$–$C_{12}$-thioether groups,
silyloxy groups $OSiR^7R^8R^9$,
halogens
or amino groups $NR^{10}R^{11}$;

$R^3$ is selected from among the following groups:
α-branched $C_3$–$C_{12}$-alkyl groups,
$C_1$–$C_{12}$-alkyl bearing one or more identical or different $C_1$–$C_{12}$-alkyl groups, halogens,
$C_1$–$C_{12}$-alkoxy groups or $C_1$–$C_{12}$-thioether groups as substituents in the α position,
$C_7$–$C_{20}$-arylalkyl,
$C_2$–$C_{10}$-alkenyl,
$C_3$–$C_{10}$-alkenylalkyl having at least one double bond, where at least one C—C double bond is conjugated with the aromatic,
$C_3$–$C_{12}$-cycloalkyl,
$C_6$–$C_{14}$-aryl,
$C_6$–$C_{14}$-aryl bearing one or more identical or different $C_1$–$C_{12}$-alkyl groups, halogens, monohalogenated or polyhalogenated $C_1$–$C_{12}$-alkyl groups, $C_1$–$C_{12}$-alkoxy groups, silyloxy groups $OSiR^7R^8R^9$, amino groups $NR^{10}R^{11}$ or $C_1$–$C_{12}$-thioether groups as substituents,
$C_1$–$C_{12}$-alkoxy groups,
$C_6$–$C_{14}$-aryloxy groups,
$C_1$–$C_{12}$-thioether groups,
silyloxy groups $OSiR^7R^8R^9$,
halogens
and amino groups $NR^{10}R^{11}$,
where in each case adjacent radicals $R^1$ to $R^4$ may together form a 5- to 8-membered ring;

$R^5$ and $R^6$ are selected independently from among
α-branched $C_3$–$C_{12}$-alkyl groups,
$C_3$–$C_{12}$-cycloalkyl groups,
$C_3$–$C_{12}$-cycloalkyl groups bearing one or more identical or different $C_1$–$C_{12}$-alkyl groups, halogens, monohalogenated or polyhalogenated $C_1$–$C_{12}$-alkyl groups, $C_1$–$C_{12}$-alkoxy groups, silyloxy groups $OSiR^7R^8R^9$, amino groups $NR^{10}R^{11}$ or $C_1$–$C_{12}$-thioether groups as substituents, X is oxygen, sulfur, selenium, N—$R^{12}$, P—$R^{12}$ or $AsR^{12}$, Y is hydrogen or
an alkali metal cation,
a $C_1$–$C_{18}$-alkylacyl anion,
a $C_6$–$C_{14}$-arylacyl anion or $SiR^7R^8R^9$, $R^7$ to $R^{12}$ are selected independently from among hydrogen, branched or unbranched $C_1$–$C_6$-alkyl groups, benzyl radicals and $C_6$–$C_{14}$-aryl groups, where in each case two adjacent radicals $R^7$ and $R^8$ or $R^{10}$ and $R^{11}$ may together form a saturated or unsaturated 5- to 8-membered ring.

2. A metal complex as claimed in claim 1, obtainable from a metal precursor of a metal M selected from the group consisting of iron, cobalt or nickel in the oxidation state 0 or palladium in the oxidation state 0 or +2, where the ligand or ligands of the metal precursor are selected from the group consisting of the following ligands:

ethylenically unsaturated double bond systems,
phosphines $R_xPH_{3-1}$
amines $R_xNH_{3-x}$,
CO,
nitriles,
halide ions,
$C_1$–$C_6$-alkyl anions,
allyl anions,
benzyl anions and
aryl anions, where
R is selected from among hydrogen, $C_1$–$C_6$-alkyl groups and $C_6$–$C_{14}$-aryl groups,
x is 0, 1, 2 or 3;

and a ligand of the formula I in which
$R^1$, $R^2$ and $R^4$ are, independently of one another:
hydrogen,
$C_1$–$C_6$-alkyl,
$C_1$–$C_6$-alkyl bearing one or more identical or different $C_1$–$C_6$-alkyl groups, halogens,
$C_1$–$C_6$-alkoxy groups or $C_1$–$C_6$-thioether groups as substituents,
$C_7$–$C_{20}$-arylalkyl,
$C_2$–$C_6$-alkenyl,
$C_5$–$C_7$-cycloalkyl,
$C_5$–$C_7$-cycloalkyl, bearing one or more identical or different $C_1$–$C_6$-alkyl groups,
halogens, $C_1$–$C_6$-alkoxy groups or $C_1$–$C_6$-thioether groups as substituents,
$C_6$–$C_{14}$-aryl,
$C_6$–$C_{14}$-aryl, bearing one or more identical or different $C_1$–$C_6$-alkyl groups, halogens,
monohalogenated or polyhalogenated $C_1$–$C_6$-alkyl groups, $C_1$–$C_6$-alkoxy groups, silyloxy groups $OSiR^7R^8R^9$, amino groups $NR^{10}R^{11}$ or $C_1$–$C_6$-thioether groups as substituents,
$C_1$–$C_6$-alkoxy groups,
$C_6$–$C_{14}$-aryloxy groups,
$C_1$–$C_6$-thioether groups,
silyloxy groups $OSiR^7R^8R^9$,
halogens
or amino groups $NR^{10}R^{11}$;

$R^3$ is selected from among the following groups:
α-branched $C_3$–$C_6$-alkyl groups, $C_1$–$C_6$-alkyl, bearing one or more identical or different halogens, $C_1$–$C_6$-alkoxy groups or $C_1$–$C_6$-thioether groups as substituents in the α-position,
$C_7$–$C_{20}$-arylalkyl,
$C_2$–$C_{10}$-alkenyl,
$C_3$–$C_{10}$-alkenylalkyl having at least one double bond conjugated with the aromatic,
$C_5$–$C_7$-cycloalkyl,
$C_5$–$C_7$-cycloalkyl, bearing one or more identical or different $C_1$–$C_6$-alkyl groups,
halogens, $C_1$–$C_6$-alkoxy groups or $C_1$–$C_6$-thioether groups as substituents,
$C_6$–$C_{14}$-aryl,
$C_6$–$C_{14}$-aryl bearing one or more identical or different $C_1$–$C_6$-alkyl groups, halogens,
monohalogenated or polyhalogenated $C_1$–$C_6$-alkyl groups, $C_1$–$C_6$-alkoxy groups, silyloxy groups $OSiR^7R^8R^9$, amino groups $NR^{10}R^{11}$ or $C_1$–$C_6$-thioether groups as substituents,
$C_1$–$C_6$-alkoxy groups,
$C_6$–$C_{14}$-aryloxy groups,
$C_1$–$C_6$-thioethet groups,
silyloxy groups $OSiR^7R^8R^9$,
halogens
and amino groups $NR^{10}R^{11}$,
where in each case adjacent radicals $R^1$ to $R^4$ may together form a 5- to 8-membered ring;

$R^5$ and $R^6$ are selected independently from among
α-branched $C_3$–$C_6$-alkyl groups,
$C_5$–$C_7$-cycloalkyl groups,
$C_5$–$C_7$-cycloalkyl groups bearing one or more identical or different $C_1$–$C_{12}$-alkyl groups,
halogens, monohalogenated or polyhalogenated $C_1$–$C_6$-alkyl groups, $C_1$–$C_6$-alkoxy groups,
silyloxy groups $OSiR^7R^8R^9$, amino groups $NR^{10}R^{11}$ or $C_1$–$C_6$-thioether groups as substituents,
benzyl radicals, X is oxygen or sulfur,
Y is hydrogen or an alkali metal cation,
a $C_1$–$C_3$-alkylacyl anion,
a $C_6$–$C_{14}$-arylacyl anion or $SiR^7R^8R^9$,
$R^7$ to $R^{11}$ are selected independently from among hydrogen, $C_1$–$C_6$-alkyl groups, benzyl radicals and $C_6$–$C_{14}$-aryl groups, where in each case two adjacent radicals $R^7$ and $R^8$ or $R^{10}$ and $R^{11}$ may together form a saturated or unsaturated 5–8-membered ring.

3. A metal complex as claimed in claim 1, obtainable from a metal precursor selected from among the compounds $Ni(C_2H_4)_3$, $Ni(1,5$-cyclooctadiene$)_2$, $Ni(1,6$-cyclodecadienene$)_2$, $Ni(1,5,9$-all-trans-cyclododecatriene$)_2$, $Pd(norbornadiene)Cl_2$, $Ni[P(C_6H_5)_3]_4$ and $Pd[P(C_6H_5)_3]_4$,
and a ligand of the formula I in which
$R^1$, $R^2$ and $R^4$ are, independently of one another:
hydrogen,
$C_1$–$C_4$-alkyl,
$C_1$–$C_4$-alkyl bearing one or more identical or different $C_1$–$C_4$-alkyl groups, halogens,
$C_1$–$C_4$-alkoxy groups or $C_1$–$C_4$-thioether groups as substituents,
benzyl,
$C_2$–$C_4$-alkenyl,
$C_5$–$C_7$-cycloalkyl,
phenyl,
phenyl bearing one or more identical or different $C_1$–$C_4$-alkyl groups, halogens,
monohalogenated or polyhalogenated $C_1$–$C_4$-alkyl groups, $C_1$–$C_4$-alkoxy groups or silyloxy groups $OSiR^7R^8R^9$ as substituents, $C_1$–$C_4$-alkoxy groups,
phenoxy,
$C_1$–$C_4$-thioether groups,
silyloxy groups $OSiR^7R^8R^9$,
halogen,
or amino groups $NR^{10}OR^{11}$;
$R^3$ is selected from among the following groups:
α-branched $C_3$–$C_6$-alkyl groups,
$C_1$–$C_4$-alkyl bearing one or more identical or different halogens or $C_1$–$C_4$-alkoxy groups as substituents in the α position,
benzyl,
$C_5$–$C_7$-cycloalkyl,
phenyl,
phenyl bearing one or more identical or different $C_1$–$C_4$-alkyl groups, halogens,
monohalogenated or polyhalogenated $C_1$–$C_4$-alkyl groups, $C_1$–$C_4$-alkoxy groups, silyloxy groups $OSiR^7R^8R^9$ or amino groups $NR^{10}R^{11}$ as substituents,
$C_1$–$C_4$-alkoxy groups,
phenoxy,
$C_1$–$C_4$-thioether groups,
silyloxy groups $OSiR^7R^8R^9$,
halogens
and amino groups $NR^{10}R^{11}$,
where in each case adjacent radicals $R^1$ to $R^4$ may together form a 5- to 8-membered ring;
$R^5$ and $R^6$ are selected independently from among
α-branched $C_3$–$C_6$-alkyl groups and
$C_5$–$C_7$-cycloalkyl groups,
X is oxygen or sulfur,
Y is hydrogen or
an alkali metal cation,
a $C_1$–$C_3$-alkylacyl anion,
a benzo cation or
$SiR^7R^8R^9$, where $R^7$ to $R^9$ are selected independently from among hydrogen, $C_1$–$C_4$-alkyl groups and phenyl groups;
$R^7$ to $R^{11}$ are selected independently from among hydrogen, $C_1$–$C_4$-alkyl groups and phenyl groups, where in each case two adjacent radicals $R^7$ and $R^8$ or $R^{10}$ and R11 may together form a saturated or unsaturated 5- to 8-membered ring.

4. A metal complex as claimed in claim 1, obtainable from $Ni(1,5\text{-dicyclooctadienyl})_2$
and a ligand of the formula I in which
$R^1$, $R^2$ and $R^4$ are, independently of one another:
hydrogen,
$C_1$–$C_4$-alkyl,
benzyl,
$C_5$–$C_7$-cycloalkyl,
phenyl,
phenyl bearing one or more identical or different $C_1$–$C_4$-alkyl groups, halogens,
monohalogenated or polyhalogenated $C_1$–$C_4$-alkyl groups, $C_1$–$C_4$-alkoxy groups or silyloxy groups $OSiR^7R^8R^9$ as substituents,
$C_1$–$C_4$-alkoxy groups,
phenoxy,
$C_1$–$C_4$-thioether groups,
silyloxy groups $OSiR^7R^8R^9$, or
halogen;
$R^3$ is selected from among the following groups:
α-branched $C_3$–$C_6$-alkyl groups,
$C_1$–$C_4$-alkyl bearing one or more identical or different halogens or $C_1$–$C_4$-alkoxy groups as substituents in the a position,
benzyl,
$C_5$–$C_7$-cycloalkyl,
phenyl,
phenyl bearing one or more identical or different $C_1$–$C_4$-alkyl groups, halogens,
monohalogenated or polyhalogenated $C_1$–$C_4$-alkyl groups, $C_1$–$C_4$-alkoxy groups or silyloxy groups $OSiR^7R^8R^9$ as substituents,
$C_1$–$C_4$-alkoxy groups,
phenoxy,
$C_1$–$C_4$-thioether groups,
silyloxy groups $OSiR^7R^8R^9$,
halogens and amino groups $NR^{10}R^{11}$,
where in each case adjacent radicals $R^1$ to $R^4$ may together form a 5- to 8-membered ring;
$R^5$ and $R^6$ are selected independently from among
α-branched $C_3$–$C_6$-alkyl groups and $C_5$–$C_7$-cycloalkyl groups,
$R^7$ to $R^{11}$ are selected independently from among hydrogen, $C_1$–$C_4$-alkyl groups and phenyl groups, where in each case two adjacent radicals $R^7$ and $R^8$ or $R^{10}$ and $R^{11}$ may together form a saturated or unsaturated 5- to 8-membered ring,
X is oxygen or sulfur and
Y is hydrogen.

5. A metal complex as claimed in claim 1, obtainable from $Ni(1,5\text{-dicyclooctadienyl})_2$
and a ligand of the formula Ia, Ia where
$R^1$ and $R^2$ are, independently of one another:
hydrogen,
$C_1$–$C_4$-alkyl, branched or unbranched,
benzyl,
$C_5$–$C_7$-cycloalkyl,
phenyl,
phenyl bearing one or more identical or different $C_1$–$C_4$-alkyl groups, halogens,
monohalogenated or polyhalogenated $C_1$–$C_4$-alkyl groups, $C_1$–$C_4$-alkoxy groups or silyloxy groups $OSiR^7R^8R^9$ as substituents,
$C_1$–$C_4$-alkoxy groups,
phenoxy,
$C_1$–$C_4$-thioether groups,
silyloxy groups $OSiR^7R^8R^9$ or
halogen;
$R^5$ and $R^6$ are selected independently from among
α-branched $C_3$–$C_{12}$-alkyl groups and $C_5$–$C_7$-cycloalkyl groups,
$R^7$ to $R^{11}$ are selected independently from among hydrogen, $C_1$–$C_4$-alkyl groups and phenyl groups, where in each case two adjacent radicals $R^7$ to $R^{11}$ may together form a saturated or unsaturated 5–8-membered ring,
Z is selected from among halogen, $C_1$–$C_4$-alkoxy and $C_1$–$C_4$-thioether groups;
X is oxygen or sulfur and
Y is hydrogen.

6. A catalyst for the polymerization of 1-olefins, comprising the metal complex defined in claim 1 immobilized on a solid support material.

7. The catalyst defined in claim 6, wherein the solid support material is selected from the group consisting of porous metal oxides, sheet silicates and solid halides.

8. A process for the polymerization of 1-olefins, which comprises bringing the metal complex defined in claim 1 into contact with one or more 1-olefins at a pressure of 1–1000 bar and a temperature of 10–250° C., and wherein the metal complex is optionally immobilized on a solid support material.

9. The process of claim 8, which is conducted at a pressure of 2–100 bar and a temperature of 40–150° C.

10. The process of claim 8, wherein the 1-olefin is ethylene.

11. The process of claim 8, wherein the metal complex is immobilized and the solid support material is selected from the group consisting of porous metal oxides, sheet silicates and solid halides.

12. The process of claim 9, wherein the metal complex is immobilized and the solid support material is selected from the group consisting of porous metal oxides, sheet silicates and solid halides.

13. The process of claim 9, wherein the 1-olefin is ethylene.

14. The process of claim 10, wherein the metal complex is immobilized and the solid support material is selected from the group consisting of porous metal oxides, sheet silicates and solid halides.

* * * * *

UNITED STATES PATENT AND TRADEMARK OFFICE
CERTIFICATE OF CORRECTION

PATENT NO. : 6,559,326 B1
DATED : May 6, 2003
INVENTOR(S) : Kristen et al.

It is certified that error appears in the above-identified patent and that said Letters Patent is hereby corrected as shown below:

Column 23,
Line 24, "$R_x$-$PH_{3-1}$" should be -- $R_x$-$PH_{3-x}$ --.

Column 24,
Line 21, "$C_1$-$C_6$-thioethet" should be -- $C_1$-$C_6$-thioether --.

Column 25,
Line 6, "$NR^{10}OR^{11}$" should be -- $NR^{10}R^{11}$ --.
Line 67, "a" should be -- $\alpha$ --.

Signed and Sealed this

Twenty-sixth Day of August, 2003

JAMES E. ROGAN
*Director of the United States Patent and Trademark Office*